United States Patent
Kim et al.

(10) Patent No.: US 10,980,824 B2
(45) Date of Patent: Apr. 20, 2021

(54) PHARMACEUTICAL COMPOSITION COMPRISING QUERCETIN-3-O-β-D-XYLOPYRANOSIDE FOR PREVENTING OR TREATING LIVER DISEASE

(71) Applicant: Hongcheon Institute of Medical Herb, Gangwon-do (KR)

(72) Inventors: Sun Young Kim, Gangwon-do (KR); Yong Jun Lee, Gangwon-do (KR); Dong Joo Kwon, Gangwon-do (KR); Young Han Kim, Gangwon-do (KR)

(73) Assignee: Hongcheon Institute of Medical Herb, Gangwon-do (KR)

( * ) Notice: Subject to any disclaimer, the term of this patent is extended or adjusted under 35 U.S.C. 154(b) by 0 days.

(21) Appl. No.: 16/470,826

(22) PCT Filed: Nov. 13, 2017

(86) PCT No.: PCT/KR2017/012772
§ 371 (c)(1),
(2) Date: Jun. 18, 2019

(87) PCT Pub. No.: WO2018/117421
PCT Pub. Date: Jun. 28, 2018

(65) Prior Publication Data
US 2019/0388449 A1 Dec. 26, 2019

(30) Foreign Application Priority Data

Dec. 23, 2016 (KR) .................. 10-2016-0178182

(51) Int. Cl.
*A61K 31/7048* (2006.01)
*A61P 1/16* (2006.01)
(52) U.S. Cl.
CPC ............ *A61K 31/7048* (2013.01); *A61P 1/16* (2018.01)
(58) Field of Classification Search
CPC ............................. A61K 31/7048; A61P 1/16
See application file for complete search history.

(56) References Cited

U.S. PATENT DOCUMENTS

2005/0147723 A1* 7/2005 Liu .................. A23B 7/02
426/489

FOREIGN PATENT DOCUMENTS

KR 10/2005/0092568 9/2005
KR 10/2006/0079498 7/2006

OTHER PUBLICATIONS

Definition of prevent, Oxford English Dictionary Online, http://dictionary.oed.com/, accessed online Mar. 27, 2010, especially definition 9a. at p. 2. (Year: 2010).*
Chen, X., Pharmacogn. Mag., 2010, 6(22), p. 135-141. (Year: 2010).*
Li et al., Biomedical Reports, 2013, 1, p. 71-76. (Year: 2013).*
Hu et al., American Journal of Chinese Medicine, 2012, 40(3), p. 599-610. (Year: 2012).*
Hamdy et al "Bioactive Phenolic Compounds from the Egyptian Red Sea Seagrass *Thalassodendron Ciliatum*" Verlag der Zeitschrift fur Naturforschung vol. 67, pp. 291-296, 2012.
Kalegari et al "Chemical Composition, Antioxidant Activity and Hepatoprotective Potential of *Rourea Inducta* Planch. (Connaraceae) Against CCl$_4$-Induced Liver Injury in Female Rats" Nutrition vol. 30, pp. 713-718, 2014.
Okoye et al "Flavonoid Glycosides from *Olax Mannii*: Structure Elucidation and Effect on the Nuclear Factor Kappa B Pathway" Journal of Ethnopharmacology vol. 176, pp. 27-34, 2015.
Soliman et al "Phytochemical and In Vitro Biological Study of *Psidium Guajava* L. Leaves Cultivated in Egypt" World Journal of Pharmacy and Pharmaceutical Sciences vol. 4, pp. 124-139, 2015.
Van der Sluis et al "An Improved, Rapid In Vitro Method to Measure Antioxidant Acitivty. Application on Selected Flavonoids and Apple Juice" Journal of Agricultural and Food Chemistry vol. 48, pp. 4116-4122, 2000.

* cited by examiner

*Primary Examiner* — Jonathan S Lau
(74) *Attorney, Agent, or Firm* — Cesari & McKenna, LLP

(57) ABSTRACT

Provided is a pharmaceutical composition including quercetin-3-O-β-D-xylopyranoside for preventing or treating a liver disease. Since the composition has an effect on inhibiting alcohol-induced accumulation of triglycerides in the blood and liver, having no toxicity and without affecting feed intake, body weight, organ weight, and the like, the composition of the present invention may be efficiently utilized as a pharmaceutical composition for preventing and treating a liver disease such as steatosis, hepatitis, hepatic fibrosis, and cirrhosis or a health functional food for preventing or alleviating a liver disease such as steatosis, hepatitis, hepatic fibrosis, and cirrhosis.

8 Claims, 11 Drawing Sheets
Specification includes a Sequence Listing.

SEQUENCE LISTING

```
<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: Fas forward primer

<400> SEQUENCE: 1
ggaggtggtg atagccggta t                                      21

<210> SEQ ID NO 2
<211> LENGTH: 21
<212> TYPE: DNA
<213> ORGANISM: Artificial Sequence
<220> FEATURE:
<223> OTHER INFORMATION: Fas reverse primer

<400> SEQUENCE: 2
```
tgggtaatcc atagagccca g                                              21

<210> SEQ ID NO 3
<211> LENGTH: 19
<212> TYPE: DNA
<213> ORGANISM: Artificial Sequence
<220> FEATURE:
<223> OTHER INFORMATION: ApoB forward primer

<400> SEQUENCE: 3
cgtgggctcc agcattcta                                                 19

<210> SEQ ID NO 4
<211> LENGTH: 22
<212> TYPE: DNA
<213> ORGANISM: Artificial Sequence
<220> FEATURE:
<223> OTHER INFORMATION: ApoB reverse primer

<400> SEQUENCE: 4
tcaccagtca tttctgcctt tg                                             22

<210> SEQ ID NO 5
<211> LENGTH: 20
<212> TYPE: DNA
<213> ORGANISM: Artificial Sequence
<220> FEATURE:
<223> OTHER INFORMATION: Cd36 forward primer

<400> SEQUENCE: 5
tggagctgtt attggtgcag                                                20

<210> SEQ ID NO 6
<211> LENGTH: 20
<212> TYPE: DNA
<213> ORGANISM: Artificial Sequence
<220> FEATURE:
<223> OTHER INFORMATION: Cd36 reverse primer

<400> SEQUENCE: 6
tgggttttgc acatcaaaga                                                20

<210> SEQ ID NO 7
<211> LENGTH: 18
<212> TYPE: DNA
<213> ORGANISM: Artificial Sequence
<220> FEATURE:
<223> OTHER INFORMATION: Fabp forward primer

<400> SEQUENCE: 7
gctgcggctg ctgtatga                                                  18

<210> SEQ ID NO 8
<211> LENGTH: 18
<212> TYPE: DNA
<213> ORGANISM: Artificial Sequence
<220> FEATURE:
<223> OTHER INFORMATION: Fabp reverse primer

<400> SEQUENCE: 8
caccggcctt ctccatga                                                  18

<210> SEQ ID NO 9
<211> LENGTH: 20
<212> TYPE: DNA
<213> ORGANISM: Artificial Sequence

```
<220> FEATURE:
<223> OTHER INFORMATION: b-actin forward primer

<400> SEQUENCE: 9
ggctgtattc ccctccatcg                                           20

<210> SEQ ID NO 10
<211> LENGTH: 22
<212> TYPE: DNA
<213> ORGANISM: Artificial Sequence
<220> FEATURE:
<223> OTHER INFORMATION: b-actin reverse primer

<400> SEQUENCE: 10
ccagttggta acaatgccat gt                                        22
```

PHARMACEUTICAL COMPOSITION COMPRISING QUERCETIN-3-O-β-D-XYLOPYRANOSIDE FOR PREVENTING OR TREATING LIVER DISEASE

CROSS-REFERENCE TO RELATED APPLICATIONS

This application is the National Stage of International Application No. PCT/KR2017/012772, filed Nov. 13, 2017, which claims priority to Korean Application No. 10-2016-0178182, filed Dec. 23, 2016. The contents of both prior applications are hereby incorporated by reference herein in their entirety.

TECHNICAL FIELD

The present invention relates to a pharmaceutical composition including quercetin-3-O-β-D-xylopyranoside for preventing or treating a liver disease, and more particularly, to a pharmaceutical composition including quercetin-3-O-β-D-xylopyranoside for preventing or treating steatosis, hepatitis, hepatic fibrosis, or cirrhosis, a health functional food including quercetin-3-O-β-D-xylopyranoside for preventing or alleviating a liver disease, and a method of preventing or treating a liver disease, the method including administering quercetin-3-O-β-D-xylopyranoside to a subject.

BACKGROUND ART

The liver is an organ having a major role in the metabolism of various nutrients, and dysfunction of the liver causes problems with nutrient metabolism in a living body. Although liver cells can recover from mild liver damage with rest, liver diseases may become more severe since the busy pace of modern society only allows very limited time for rest. Although liver diseases are currently treated by drugs in combination with exercise, abstinence from alcohol, dietary therapy, and the like, they are difficult to completely cure, and thus there is a need to continuously develop effective and improved therapeutic agents for liver diseases or hepatoprotective agents.

With metabolic syndromes such as obesity and type 2 diabetes becoming more common, liver diseases caused by fatty liver are increasing. Among these, steatosis (fatty liver disease) is induced as fat is accumulated in the liver due to excess intake of fat or alcohol, increases in fat synthesis, decreases in export and combustion of triglycerides, etc. In general, steatosis is defined as when intrahepatic fat accounts for 5% or more of liver weight. Steatosis and steatohepatitis are regarded as subtypes of chronic fatty liver diseases and may progress to liver cirrhosis, resulting in hepatocellular carcinoma (HCC) as it becomes worse. Most of the fats accumulated in the fatty liver are triglycerides. Particularly, alcoholic fatty liver is caused by an increase in synthesis of fats in the liver and a disorder in energy metabolism due to excess intake of alcohol, pathophysiologically resulting in apoptosis, necrosis, and necrotic inflammation as well as intrahepatic fibrosis. This is because the liver is a major organ responsible for the metabolism, digestion, and detoxification of ingested ethanol, and most ethanol metabolism occurs in the liver. Although some believe that fatty liver disease is merely the accumulation of fat in the liver, it is accompanied by liver damage, liver inflammation, and liver fat accumulation with rare clinical symptoms, such that fatty liver disease is called a silent disease. Considering that 50% of patients diagnosed with alcoholic steatosis develop cirrhosis, steatosis should be considered as one of the most severe liver diseases.

No therapeutic agent capable of preventing progression of steatosis to cirrhosis has yet been developed. Although there have been efforts to develop therapeutic agents for associated diseases, such as metabolic syndrome, hypertension, cardiovascular disease, and type 2 diabetes, due to the side effects thereof, exercise and diet therapies have been recommended as alternatives. In fact, due to the low therapeutic effects of these methods in treating steatosis, there is a need to develop effective therapeutic agents. It has been reported that some hypoglycemic agents such as metformin have therapeutic effects on steatosis based on the verification that steatosis is associated with insulin resistance in cells observed in diabetic and obese states. However, there is a problem in that such drugs cause side effects such as liver toxicity or lactic acidosis. Also, it has been reported that pioglitazone, a drug for reducing insulin resistance and oxidative stress, and thiazolidinedione, a drug for diabetes which raises adiponectin levels, have effects on improving hepatic insulin sensitivity together with effects on inhibiting liver damage in patients with steatosis, such that there is a possibility of developing these drugs to treat steatosis. However, a severe adverse effect (SAE), which may affect the fatality of patients, was observed at the optimal effective concentration. In addition, although betaine, glucuronate, methionine, choline, and lipotrophic preparations have been used in adjuvant therapy, the medical basis for their use has not been fully proved. Therefore, there is an urgent need to develop safe therapeutic agents for steatosis which are superior in efficacy and derived from natural products without causing side effects.

Among liver diseases, hepatitis is the inflammation of liver cells and liver tissue, a major cause of which is heavy alcohol consumption. Alcoholic hepatitis is a type of acute hepatitis that occurs mostly due to binge drinking, i.e., drinking too much alcohol in a short period of time. Heavy drinking increases the permeability of intestinal mucosa, resulting in the introduction of enterobacteria into the bloodstream of the portal vein. Endotoxin and lipopolysaccharide (LPS) excreted by the enterobacteria enter the liver and bind to a specific receptor (Toll-like receptor 4) located on the surface of Kupffer cells. Subsequently, cytokines such as TNF-α are released via intracellular signaling pathways to cause apoptosis, necrosis, and inflammation of liver cells.

A primary mechanism of alcoholic hepatitis is immune response. Although total abstinence from alcohol may be enough for recovery from mild alcoholic hepatitis, severe alcoholic hepatitis can be a life-threatening disease, with about 40% to 50% of deaths without therapeutic treatment. Treatment of severe alcoholic hepatitis requires suppression of immune response. For this purpose, steroids, inhibitors of immune response, and pentoxifylline, an inhibitor of TNF-α, are currently approved and in clinical trials. Since steroids have many adverse effects and limitations, pentoxifylline is now preferred for the treatment of severe alcoholic hepatitis. However, the therapeutic effects of pentoxifylline are not satisfactory.

Meanwhile, among the liver diseases, hepatic fibrosis refers to a disease caused by fibrosis developing in the liver. After liver tissue is damaged by various stresses in the human body, various cytokines, such as transforming growth factor beta (TGF-β), secreted from Kupffer cells activate hepatic stellate cells. The secreted TGF-β promotes the synthesis of collagen, causing accumulation of the extracellular matrix and resulting in fibrosis in the liver. In particularly, progression from simple steatosis to fibrosis involves not only liver damage but also immunological and genetic factors. The pathway of the immunological pathogenesis is the hedgehog (HH) pathway. Hedgehog-related proteins are signaling substances inducing immune responses in liver cells. Activity of the hedgehog induces natural killer cells and promotes hepatic fibrosis by increasing the levels of inflammatory cytokines.

When hepatic fibrosis continues to progress, cirrhosis develops. Caused by persistent and repetitive diffuse parenchymal liver damage, increases in fibrous tissue, and hepatic nodes formed by regeneration of liver cells, cirrhosis is a chronic disease pathologically accompanied by necrosis, inflammation, and fibrosis, and patients with hepatic cirrhosis also experience clinical symptoms such as fluid retention, muscle wasting, intestinal bleeding, and liver failure, resulting in cirrhosis complications and hepatocellular carcinoma and eventually leading to death.

Since there is no awareness at an early stage of development of hepatic fibrosis and cirrhosis, and because these diseases are found only after having progressed considerably, extensive research has been conducted to develop methods of rapidly diagnosing and treating hepatic fibrosis and cirrhosis. For example, Korean Patent No. 1086040 discloses a therapeutic agent including an asiatic acid derivative, a pharmaceutically acceptable salt thereof, or an ester thereof for treating hepatic fibrosis and cirrhosis, and Korean Patent No. 1135574 discloses a technique for preventing and treating hepatic fibrosis, cirrhosis, and the like by using N-(2,2-disubstituted-2H-cromene-6-yl) thiourea derivatives. However, therapeutic agents derived from natural products and having effects in the treatment of hepatic fibrosis without cytotoxicity have not yet been sufficiently developed.

DESCRIPTION OF EMBODIMENTS

Technical Problem

The present inventors have made intensive efforts to solve the above-described problems and have found that quercetin-3-O-β-D-xylopyranoside extracted and separated from East Asian strip maple is effective for preventing and treating a liver disease such as steatosis, hepatitis, hepatic fibrosis, or cirrhosis by suppressing alcohol-induced accumulation of triglycerides in the blood and liver, having no cytotoxicity and without affecting feed intake, body weight, organ weight, and the like, thereby completing the present invention.

Solution to Problem

An object of the present invention is to provide a pharmaceutical composition including quercetin-3-O-β-D-xylopyranoside for preventing or treating a liver disease.

In particular, the object of the present invention is to provide a pharmaceutical composition including quercetin-3-O-β-D-xylopyranoside for preventing or treating steatosis, hepatitis, hepatic fibrosis, or cirrhosis.

Another object of the present invention is to provide a health functional food including quercetin-3-O-β-D-xylopyranoside for preventing or alleviating a liver disease.

Another object of the present invention is to provide a method of preventing or treating a liver disease, the method including administering quercetin-3-O-β-D-xylopyranoside to a subject.

Advantageous Effects of Disclosure

A composition including quercetin-3-O-β-D-xylopyranoside according to the present invention may be efficiently used as a pharmaceutical composition for preventing or treating steatosis, hepatitis, hepatic fibrosis, and cirrhosis or a health functional food for preventing or alleviating steatosis, hepatitis, hepatic fibrosis, and cirrhosis since the composition suppresses alcohol-induced triglyceride accumulation in the blood and liver while being free of toxicity and without affecting feed intake, body weight, organ weight, and the like.

BEST MODE

Hereinafter, the present invention will be described in detail. Meanwhile, each description and embodiment disclosed in the present invention may be applied herein to describe different descriptions and embodiments. In other words, all combinations of various components disclosed in the present invention are included within the scope of the present invention. Furthermore, the scope of the present invention should not be limited by the detailed description provided below.

According to an aspect of the present invention, provided is a pharmaceutical composition including quercetin-3-O-β-D-xylopyranoside for preventing or treating a liver disease.

As used herein, the "quercetin-3-O-β-D-xylopyranoside" is a compound represented by Formula 1 below and having a chemical formula of $C_{20}H_{18}O_{11}$ and a molecular weight of 302.23. Quercetin-3-O-β-D-xylopyranoside is known to be extracted from East Asian strip maple and dissolved in a solvent such as pyrimidine and methanol. Although antidiabetic activity, antioxidant activity, and the like thereof have been known, preventive or therapeutic effects thereof on a liver disease have not yet been reported.

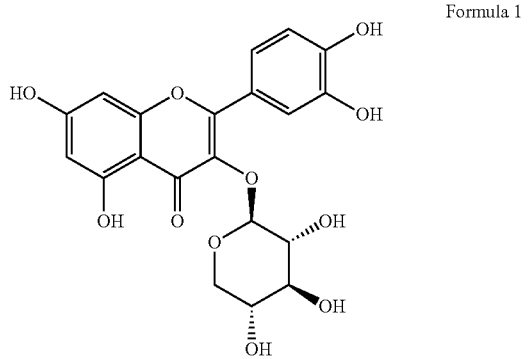 [SMILES: O=c1c(O[C@@H]2OC[C@@H](O)[C@H](O)[C@H]2O)c(-c2ccc(O)c(O)c2)oc2cc(O)cc(O)c12]

Formula 1

As a result of administering the quercetin-3-O-β-D-xylopyranoside to mice according to an embodiment of the present invention, it was identified that feed intake, body weight, and organ weight were not affected thereby and that it had no cytotoxicity, and thus the quercetin-3-O-β-D-xylopyranoside is confirmed as a safe compound derived from a natural product (FIGS. 1 to 4).

As used herein, the "liver disease" refers to the inability of the liver to normally perform metabolism because of a failure in at least one of various functions that the liver performs.

An increase in CYP2E1 by alcohol or the like induces oxidative stress, and tumor necrosis factor-alpha (TNF-α) induced thereby contributes to damage to liver cell damage. Due to damaged liver cells, blood concentrations of aminotransferases such as alanine aminotransferase (ALT) and aspartate aminotransferase (AST) are increased. Thus, the effects of preventing and treating a liver disease and the effect of protecting the liver may be confirmed by measuring the blood concentrations of ALT and AST.

Figure 10:
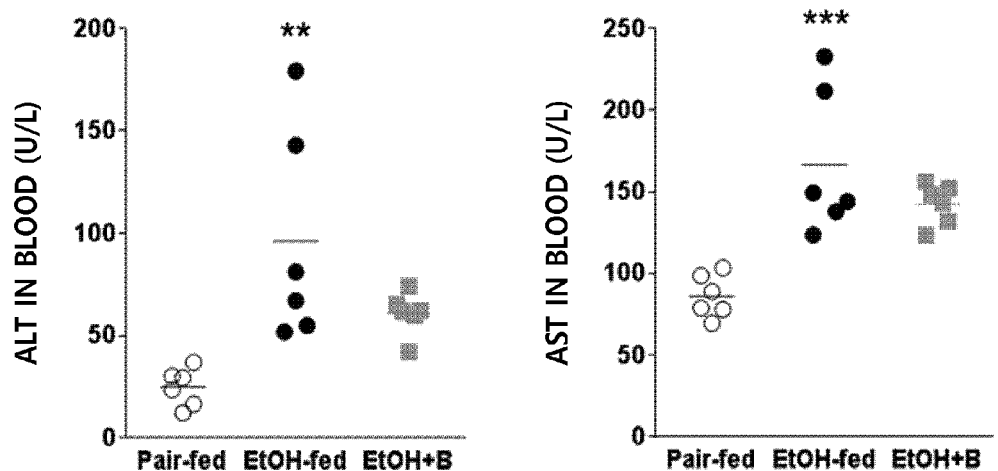
FIG. 10 is a graph illustrating biochemical analysis results of ALT and AST levels in the blood of alcoholic fatty liver-induced mice and control mice.

In an embodiment of the present invention, as a result of measuring ALT and AST levels, which are indicators of liver cell damage, in the blood and liver tissue, it was confirmed that the ALT and AST levels of a group administered with quercetin-3-O-β-D-xylopyranoside were lower than those of a control group (FIG. 10). Therefore, it was confirmed that the quercetin-3-O-β-D-xylopyranoside had the hepatoprotective effect.

As used herein, the liver disease may be any disease treated by using a composition including quercetin-3-O-β-D-xylopyranoside without limitation, and examples of the liver disease may include hepatitis, hepatotoxicity, cholestasis, steatosis, hepatic fibrosis, cirrhosis, hepatic ischemia, alcoholic liver disease, liver abscess, hepatic coma, hepatatrophy, and hepatocellular carcinoma. More particularly, the disease may be steatosis, hepatitis, hepatic fibrosis, or cirrhosis.

Throughout the specification, the "steatosis" refers to a liver disease caused by accumulation of fat in the liver resulting from overconsumption of fat or alcohol, increased fat synthesis in the liver, decreased export and combustion of triglycerides, and the like, and is generally defined as intrahepatic fat of 5% or more. Particularly, "alcoholic steatosis" is caused by the excessive intake of alcohol resulting in promotion of fat synthesis in the liver, thereby causing a disorder in the process of energy metabolism.

Figure 6:
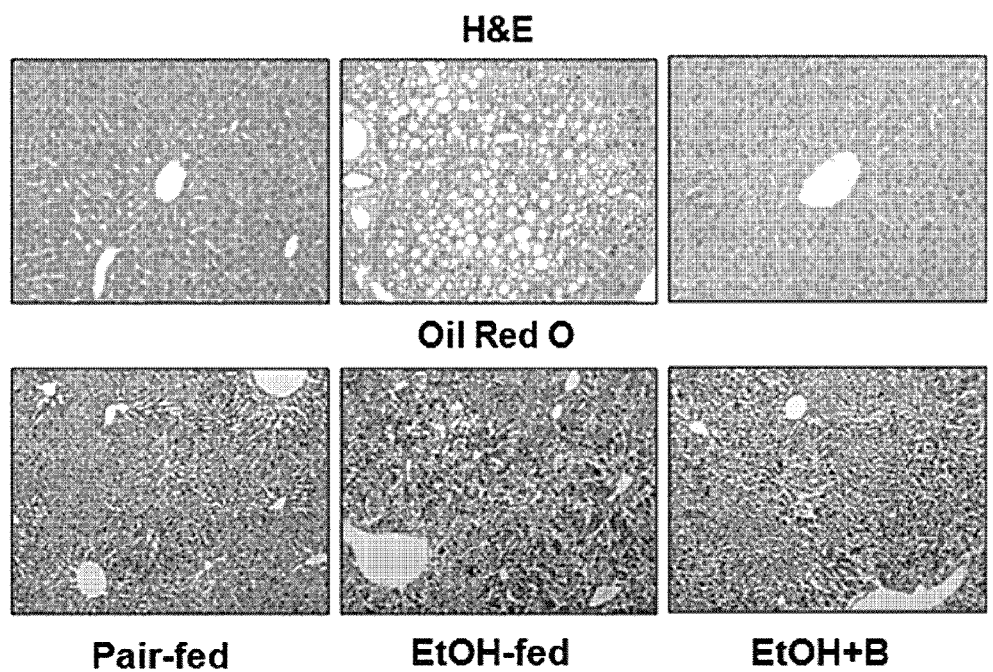
FIG. 6 shows photographs of alcoholic fatty liver-induced mice and control mice to identify the degree of triglyceride accumulation in liver tissue by H&E staining and Oil Red O staining.
Figure 7:
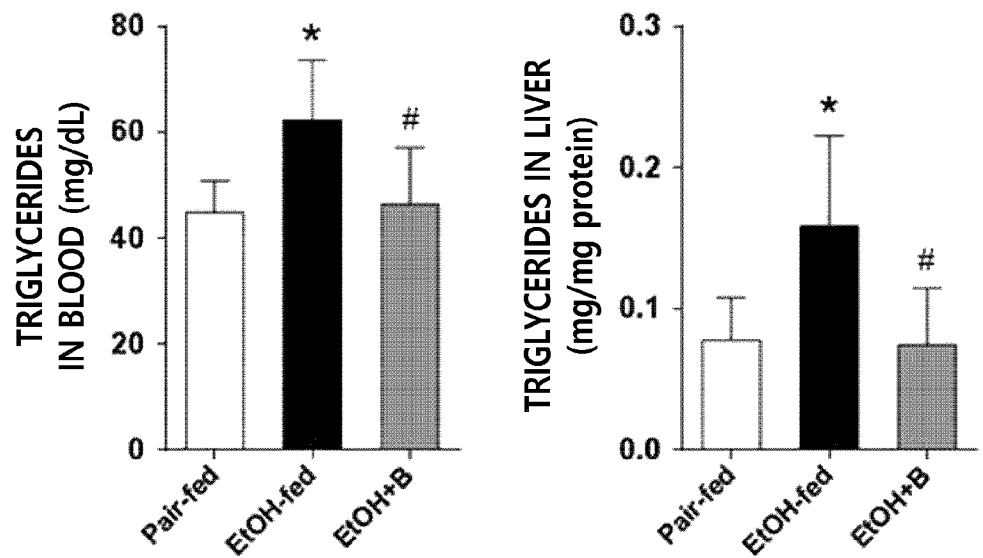
FIG. 7 is a graph illustrating concentrations of triglycerides in the blood and liver tissue of alcoholic fatty liver-induced mice and control mice for comparison therebetween.

In an embodiment of the present invention, as a result of administering the quercetin-3-O-β-D-xylopyranoside to mice, it was confirmed by visual observation that an amount of fat accumulated in the liver was significantly reduced (FIG. 5), an amount of lipid droplets accumulated in liver tissue resulting from alcohol intake was considerably reduced (FIG. 6), and concentrations of triglycerides in the blood and the liver were reduced (FIG. 7). Therefore, it was confirmed that the quercetin-3-O-β-D-xylopyranoside had preventive and therapeutic effects on steatosis.

As used herein, the "hepatitis" refers to inflammation of liver cells and liver tissue caused by excessive intake of alcohol and involving apoptosis, necrosis, and inflammatory response of liver cells. Although about 90% of ethanol is primarily oxidized into acetaldehyde by alcohol dehydrogenase (ADH), which accelerates oxidation of alcohol in the liver, cytochrome P-450 2E1 (CYP2E1) enzyme increases due to long-term exposure to alcohol, thereby inducing metabolic stress. As a result, increased GSH and GGT levels induce inflammation, resulting in damage to liver cells. More particularly, CYP2E1, as an enzyme having an important role in the microsomal ethanol oxidizing system (MEOS), promotes oxidation of ethanol, damaging the liver more severely than a catalase and ADH pathway and leading to hepatitis. Thus, it is known that when mice not having CYP2E1 are fed alcohol, liver damage may be prevented.

Figure 8:
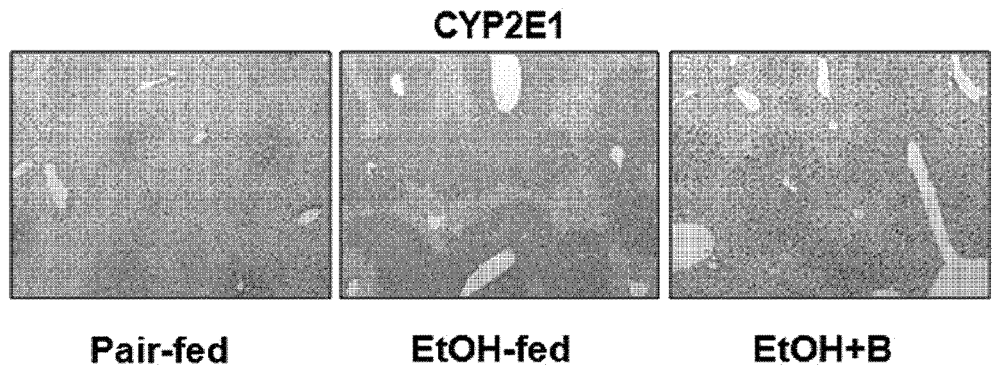
FIG. 8 shows photographs of alcoholic fatty liver-induced mice and a control mouse to identify expression of cytochrome P-450 2E1 (CYP2E1) by tissue staining.

In an embodiment of the present invention, as a result of administering the quercetin-3-O-β-D-xylopyranoside to mice to identify an expression level of the CYP2E1 enzyme, it was confirmed that the expression level of CYP2E1 was further reduced in a group treated with the quercetin-3-O-β-D-xylopyranoside, compared to a control group (FIG. 8). Therefore, it was confirmed that the quercetin-3-O-β-D-xylopyranoside had preventive and therapeutic effects on hepatitis.

The "hepatic fibrosis" is a fibrotic disease caused by damage to liver tissue by various stresses and may progress into cirrhosis when the fibrosis continues. It is known that the hepatic fibrosis progresses as levels of protein fibers of liver tissue consisting of collagenic fibers, reticular fibers, and elastic fibers increase due to alcohol.

The "cirrhosis" refers to deterioration of liver function caused by replacement of normal liver tissue with fibrous tissue such as regenerative nodules due to chronic inflammation. Particularly, cirrhosis is known to develop as the hepatic fibrosis progresses, and may further progress to diseases such as cirrhosis complications and hepatocellular carcinoma.

Figure 9:
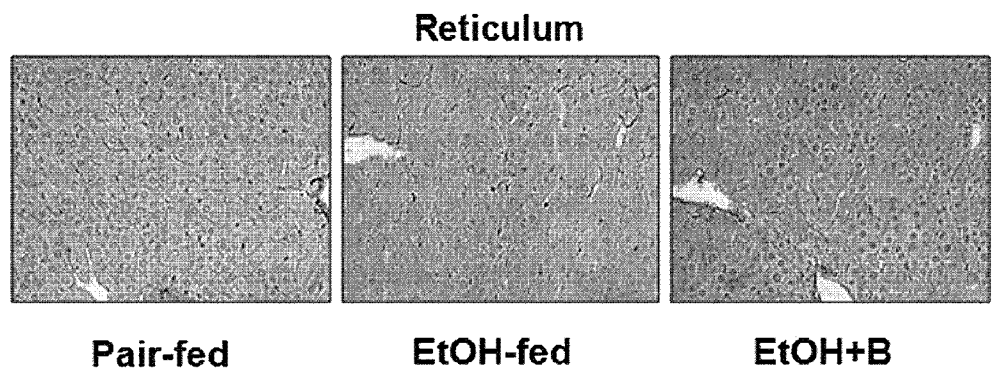
FIG. 9 shows photographs of alcoholic fatty liver-induced mice and a control mouse to identify the progression degree of hepatic fibrosis by tissue staining.

In an embodiment of the present invention, as a result of evaluating the degree of progression of hepatic fibrosis in reticular fibers by tissue staining using Gomori Reticulum, it was identified that the degree of progression of hepatic fibrosis was significantly reduced in the reticular fibers of a group administered with quercetin-3-O-β-D-xylopyranoside, compared to a control group (FIG. 9). Therefore, it was confirmed that quercetin-3-O-β-D-xylopyranoside had preventive and therapeutic effects on hepatic fibrosis and cirrhosis.

In the present invention, the prevention or treatment of the liver disease may be achieved by inhibiting accumulation of fat in the liver and suppressing expression of genes related to intrahepatic lipid metabolism.

Regarding inhibition of accumulation of fat in the liver, as a result of administering quercetin-3-O-β-D-xylopyranoside to mice according to an embodiment of the present invention, it was confirmed by visual observation that the amount of fat accumulated in the liver was significantly reduced (FIG. 5), the amount of lipid droplets accumulated in liver tissue resulting from alcohol intake was considerably reduced (FIG. 6), and a concentration of triglycerides in the liver was reduced (FIG. 7). Therefore, it was confirmed that quercetin-3-O-β-D-xylopyranoside had preventive and therapeutic effects on a liver disease such as steatosis, hepatitis, hepatic fibrosis, or cirrhosis by inhibiting accumulation of fat in the liver.

As used herein, the "gene related to intrahepatic lipid metabolism" refers to a gene involved in synthesis or accumulation of lipid components in liver cells, for example, Fas gene, ApoB gene, Cd36 gene, or Fabp gene, but is not limited thereto. Fas gene is a gene involved in synthesis of fatty acid synthase (FAS), and ApoB gene is a gene involved in synthesis of Apolipoprotein B (ApoB). Cd36 gene is a gene involved in synthesis of cluster of differentiation 36 (CD36), also known as FAT, and Fabp gene is a gene involved in synthesis of fatty acid-binding protein (FABP). Since proteins in a living body synthesized by the genes are involved in synthesis and accumulation of lipids in a cell or tissue, intrahepatic lipid accumulation may be suppressed by inhibiting the expression of the genes in the liver cell.

In an embodiment of the present invention, as a result of measuring the expressions of mRNAs of the genes related to intrahepatic lipid metabolism after administering quercetin-3-O-β-D-xylopyranoside to mice, it was confirmed that quercetin-3-O-β-D-xylopyranoside has positive effects on intrahepatic lipid metabolism and functions of mitochondria by inhibiting the expressions of the Fas, ApoB, Cd36, and Fabp genes, which are related to intrahepatic lipid metabolism (FIG. 11), thereby preventing and treating steatosis, hepatitis, hepatic fibrosis, and cirrhosis.

The quercetin-3-O-β-D-xylopyranoside may be derived from East Asian strip maple. East Asian strip maple (*Acer tegmentosum maxim.*) is a deciduous small tree in the family Aceraceae, order Sapindales, and class Dicotyledoneae.

As used herein, the term "prevention" or "preventing" means all actions that inhibit or delay the onset of a liver disease such as steatosis, hepatitis, hepatic fibrosis, and cirrhosis by administering a composition including quercetin-3-O-β-D-xylopyranoside according to the present invention. As used herein, the term "treatment" or "treating" means all actions intended to ameliorate or beneficially change a symptom associated with the liver disease by administering a composition including the quercetin-3-O-β-D-xylopyranoside.

The composition including the quercetin-3-O-β-D-xylopyranoside according to the present invention may further include at least one type of active ingredient having the same or similar functions.

The pharmaceutical composition of the present invention may be formulated into tablets, pills, powders, granules, capsules, suspensions, liquids for internal use, emulsions, syrups, aerosols, sterile injection solutions, and the like according to any method commonly used in the art to prevent or treat a liver disease.

Solid preparations for oral dosage include tablets, pills, powders, granules, capsules, and the like and are formulated by admixing at least one excipient, such as starch, calcium carbonate, sucrose, lactose, and gelatin with the active ingredient. In addition, a lubricant such as magnesium stearate and talc may be used in addition to a simple excipient. Liquid preparations for oral dosage include suspensions, liquids for internal use, emulsions, syrups, and the like. In addition to a simple diluent such as water or liquid paraffin, various excipients such as humectants, sweeteners, aromatics, and preservatives may be contained in the liquid preparations.

Preparations for parenteral dosage include sterile aqueous solutions, non-aqueous solvents, suspensions, emulsions, lyophilizates, suppositories, and the like. Propylene glycol, polyethylene glycol, vegetable oils such as olive oil, and injectable esters such as ethyl oleate may be suitable for the non-aqueous solvents and suspensions.

Also, the pharmaceutical composition of the present invention may further include a carrier, an excipient, or a diluent. Examples of the carrier, the excipient, or the diluent may include lactose, dextrose, sucrose, sorbitol, mannitol, xylitol, erythritol, maltitol, starch, Acacia rubber, alginate, gelatin, calcium phosphate, calcium silicate, cellulose, methyl cellulose, hydroxy propyl methyl cellulose, amorphous cellulose, polyvinyl pyrrolidone, water, methyl hydroxy benzoate, propyl hydroxy benzoate, propyl hydroxy benzoate, talc, magnesium stearate, silicon dioxide, and mineral oils.

A dosage of the pharmaceutical composition according to the present invention may be appropriately selected by one of ordinary skill in the art according to factors such as a preparation method, health status, body weight, gender, age of a patient, severity of disease, drug type, administration route and duration, excretion rate, and susceptibility to the reaction. The scope of the present invention is not limited by the dosage and the number of administrations.

The pharmaceutical composition of the present invention may be administered to mammals such as rats, mice, livestock, and humans via various routes. All of the administration methods are predictable, and may be, for example, oral administration, intravenous injection, intramuscular injection, or subcutaneous injection.

According to another aspect of the present invention, provided is a health functional food including quercetin-3-O-β-D-xylopyranoside for preventing or alleviating a liver disease.

The quercetin-3-O-β-D-xylopyranoside, the liver disease, and the preventing are as described above.

The term "alleviation" or "alleviating", as used herein, refers to all actions that ameliorate or beneficially change symptoms associated with a liver disease by administering the composition of the present invention.

As used herein, the "health functional food" refers to a food including raw materials or ingredients beneficial to the human body and prepared into formulations such as tablets, capsules, powders, granules, liquids, and pills. In this regard, the term "functional" means controlling of nutrients for structures and functions of the human body or obtaining beneficial effects in hygienic use such as in physiological functions. The health functional food of the present invention may be prepared by a method commonly used in the art, and raw materials and ingredients typically used in the art may be added thereto for the prevention of the health functional food. In addition, the health functional food may be prepared into any formulation that is regarded as a health functional food without limitation.

The form of the health functional food according to the present invention is not limited, and the health functional food may include all food types commonly used in the art and may be used interchangeably with any known term in the art such as functional food. In addition, the health functional food of the present invention may be prepared by mixing with any suitable auxiliary ingredients and known additives that may be contained in food and appropriately selected by one of ordinary skill in the art. Examples of the food to which the suitable auxiliary ingredients and the additives may be added may include meats, sausages, breads, chocolates, candies, snacks, cookies, pizzas, ramen, other noodles, gums, dairy products including ice cream, various kinds of soups, beverages, teas, drinks, alcoholic beverages, and vitamin complexes, and may also include foods used as animal feeds.

Figure 11:
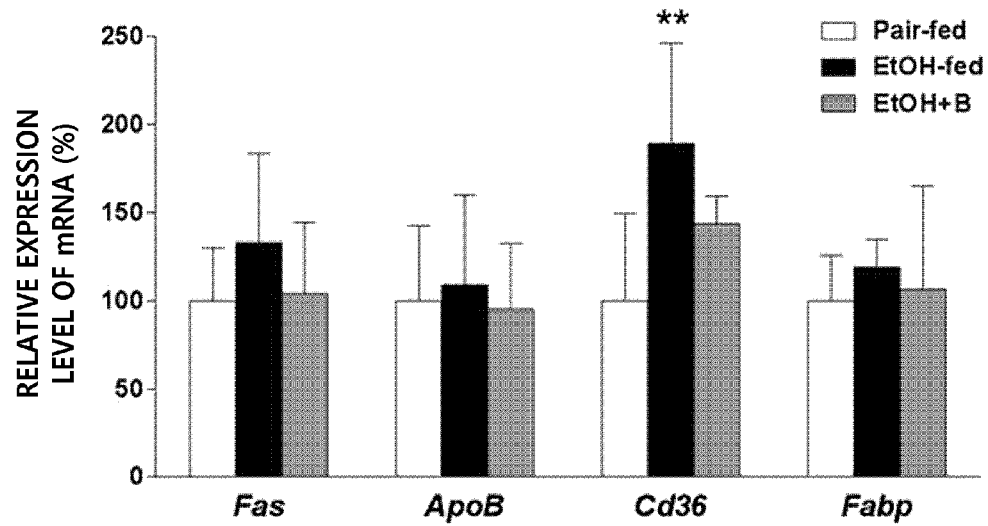
FIG. 11 is a graph illustrating expression levels of genes related to lipid metabolism in the liver.

In an embodiment of the present invention, as a result of treating mice with the quercetin-3-O-β-D-xylopyranoside according to an embodiment of the present invention, it was identified that no cytotoxicity was observed without changing the feed intake, body weight, and organ weight (FIGS. 1 to 4), the amounts of lipids and triglycerides accumulated in the liver were reduced (FIGS. 5 to 7), the expression level of the CYP2E1 enzyme was reduced (FIG. 8), the degree of progression of fibrosis in the reticular fibers was suppressed (FIG. 9), the blood concentrations of AST and ALT were reduced (FIG. 10), and the expression of genes related to intrahepatic lipid metabolism was inhibited (FIG. 11). Therefore, it was confirmed that the composition including quercetin-3-O-β-D-xylopyranoside may be used as a health functional food for preventing or alleviating a liver disease.

According to another aspect of the present invention, provided is a method of preventing or treating a liver disease including administering quercetin-3-O-β-D-xylopyranoside to a subject.

The quercetin-3-O-β-D-xylopyranoside, the liver disease, the preventing, and the treating are as described above.

As used herein, the term "subject" refers to all animals including humans, which have or are at risk of having onset of a liver disease. The animals may include humans as well as mammals such as cows, horses, sheep, pigs, goats, camels, antelopes, dogs, and cats in need of treating symptoms similar to a liver disease. The animals may refer to animals other than humans, but are not limited thereto.

The term "administration" or "administrating", as used herein, refers to introduction of the pharmaceutical composition of the present invention into a patient by an appropriate method, and the composition of the present invention may be administered via various routes such as an oral or parenteral route as long as it is able to reach a target tissue.

The method of preventing or treating a liver disease according to the present invention may include administering the composition into a subject who has or is at risk of having onset of the liver disease in a pharmaceutically effective amount.

The composition for preventing or treating a liver disease according to the present invention may be administered in the form of a pharmaceutically acceptable salt and may be used alone or in combination with a different pharmaceutically active compound as well as in an appropriate set.

The composition of the present invention may be administered orally or parenterally according to a desired method. When parenterally administered, transdermal administration, intraperitoneal injection, rectal injection, subcutaneous injection, intravenous injection, intramuscular injection, or intrathoracic injection may be used. A dosage may be appropriately adjusted according to body weight, age, gender, or health status of a patient, diet, administration time, administration route, excretion rate, severity of disease, or the like.

The dosage of the composition of the present invention may vary according to body weight, age, gender, or health status of a patient, diet, administration time, administration route, excretion rate, severity of disease, or the like. A daily dose may be from 0.0001 mg/kg to 100 mg/kg, particularly, from 0.001 mg/kg to 10 mg/kg, based on an amount of an extract mixture of the present invention, and the composition may be administered once to six times per day, but is not limited thereto.

In an embodiment of the present invention, as a result of treating mice with the quercetin-3-O-β-D-xylopyranoside, it was identified that no cytotoxicity was observed without changing the feed intake, body weight, and organ weight (FIGS. 1 to 4), the amounts of lipids and triglycerides accumulated in the liver were reduced (FIGS. 5 to 7), the expression level of the CYP2E1 enzyme was reduced (FIG. 8), the degree of progression of fibrosis in the reticular fibers was suppressed (FIG. 9), the blood concentrations of AST and ALT were reduced (FIG. 10), and the expression of genes related to intrahepatic lipid metabolism was inhibited (FIG. 11). Therefore, the effects of the composition including the quercetin-3-O-β-D-xylopyranoside on preventing or treating a liver disease were confirmed when the composition was administered to a subject.

According to another aspect of the present invention, provided is a use of quercetin-3-O-β-D-xylopyranoside for preventing or treating a liver disease.

According to another aspect of the present invention, provided is a use of quercetin-3-O-β-D-xylopyranoside for manufacturing a drug for preventing or treating a liver disease.

The quercetin-3-O-β-D-xylopyranoside, the liver disease, the preventing, and the treating are as described above.

Due to a great effect on preventing or treating a liver disease, the composition including quercetin-3-O-β-D-xylopyranoside according to the present invention may be provided for a use of manufacturing a drug for preventing or treating a liver disease.

Mode of Disclosure

Hereinafter, the present invention will be described in more detail with reference to the following examples. However, these examples are for illustrative purposes only and are not intended to limit the scope of the present invention.

Example 1: Preparation of Animal for Experiment and Construction of Alcoholic Steatosis Animal Model (NIAAA Model)

8-week-old C57BL/6N mice were purchased from DAE-HAN BIOLINK to be used for efficacy evaluation and quarantined and acclimated in a vivarium of HONGCHEON INSTITUTE OF MEDICAL HERB for 7 days (relative temperature: 23±2° C., relative humidity: 50±5%, and a 12 h light-dark cycle) prior to the start of experimentation. Among them, 18 male mice with no abnormal symptoms were selected and used.

An alcoholic steatosis animal model suggested by the National Institute on Alcohol Abuse and Alcoholism (NIAAA), as part of the U.S. National Institutes of Health (NIH), was used.

During a liquid diet adaptation period, a control group was restrictedly fed with a Lieber-DeCarli'82 control liquid diet (F1259SP, Bio-serv), and an alcohol-fed group was restrictedly fed with a Lieber-DeCarli'82 ethanol liquid diet (F1258SP, Bio-serv) using a Liquid diet feeding tube (9019, Bio-serv), and the diets were replaced with new ones at a preset time between 3 P.M. and 5 P.M.

After 5 days of the liquid diet adaptation period, the mice were orally administered with 1 mg/kg of quercetin-3-O-β-D-xylopyranoside (test substance) for 10 days and fed with a 5% alcohol liquid diet. At $11^{th}$ day, between 7 A.M. and 9 A.M., a group not fed with alcohol (hereinafter referred to as Pair-fed group) was orally administered with a 45% maltose dextrin solution, and a group fed with a 5% liquid diet (hereinafter referred to as EtOH-fed) and a group administered with a test substance (hereinafter referred to as EtOH+B group) were orally fed with 31.5% ethanol.

Example 2: Analysis Index and Analysis Method 2-1. Measurement of Body Weight of Mice and Weight of Excised Organ Alcoholic steatosis-induced mice were weighed once a day using a scale (AND FX-2000i, Korea) to evaluate changes in body weight by administration of a test substance, and starving was not performed before measuring the body weights. In addition, organs were excised and weighed to evaluate changes in weight of each of the excised organs (liver, spleen, kidney, and epididymal fat) as described in Example 2-3 below.

2-2. Hematoxylin & Eosin (H&E) Staining

Hematoxylin & Eosin (H&E) staining was performed to observe the overall shape of liver tissue and the degree of lipid accumulation in liver tissue. Specifically, the nuclei were first stained with a Harris hematoxylin staining solution for 5 minutes, and then counterstained with an Eosin solution.

2-3. Blood Sampling of Mice, Excision of Tissue and Organ, and Extraction of Lipid After 9 hours from administration of the test substance, blood samples of the mice were collected under isoflurane inhalation anesthesia, and biochemical analysis was conducted thereon. Specifically, hematological analysis of the alcoholic steatosis-induced mice was conducted using a biochemical analyzer (Kornelab20XT, Thermo, USA).

Also, after 9 hours from administration of the test substance, liver tissue and organs or tissue (epididymal fat, spleen, and kidney) were each excised under isoflurane inhalation anesthesia. The degree of fat accumulation in liver cells was observed by staining nuclei and cytoplasm by the H&E staining, and changes in weight of the other organs were observed to evaluate the effects of reducing toxicity and body fat.

2-4. Staining of Cytochrome P450 2E1 and Gomori Reticulum Staining

Reticulin fibers were stained in tissue by using a silver impregnation method including removing argyrophilic substances other than reticulin fibers, sensitizing the tissue, and impregnating the tissue with a silver solution. Meanwhile, according to immunohistochemical analysis, anti-Cytochrome P450 2E1 (ab28146, Abcam, USA) was used as a primary antibody, and the tissue was stained with a Rabbit specific HRP/DAB (ABC) Detection IHC Kit (ab64261, Abcam, USA) and counterstained with hematoxylin.

2-5. Cryostatic Sectioning and Oil Red O Staining of Liver Tissue

Isolated liver tissue was fixed in 10% NBF and immersed in a 30% sucrose solution. After washing the tissue with a PBS solution, moisture was removed therefrom, and the tissue was fixed in an optical cutting temperature (O.C.T.) compound (SAKURA, USA) as a cryostatic section embedding medium to prepare a cryostatic section block. The liver tissue was cut into 7 μm using a cryostat (Leica) and quickly attached to a slide, and the slide was kept in a deep freezer at −70° C. 5 g/L of Oil Red 0 (Sigma, USA) powder was added to 100% propylene glycol, heated, and filtered with a Whatman filter. After being kept at room temperature for one day, the Oil Red 0 was filtered and used for staining. The slide stored in the deep freezer at −70° C. was taken out immediately before an experiment, dried at room temperature for about 1 hour, washed with water, and washed with anhydrous propylene glycol for 2 minutes. The slide was immersed in the filtered Oil Red 0 for 1 hour for staining and then immersed in 85% propylene glycol for 1 hour for decolorization. The slide was washed again with running water for 5 minutes, stained with hematoxylin (H9627, Sigma, USA) for 10 seconds, and then washed with water again. After staining, the liver tissue was sealed with a Faramount Aqueous Mounting Medium (Dako, 53025, Japan).

The liver tissue was observed using an optical microscope (Axiovert40, Zeiss, Germany)

2-6. Preparation of Liver Tissue Paraffin Sample

Tissue samples were prepared by paraffin infiltration. Specifically, the livers of the mice were excised, fixed in 10% NBF for 24 hours, dehydrated with ethanol, and then subjected to a 3-stage process of making the tissue transparent using xylene. Subsequently, a paraffin block was prepared via an infiltration process and an embedding process in liquid paraffin (60° C.). The tissue block was cut to a slice having a thickness of 5 μm using a microtome and dried in a slide dryer at 60° C. for 1 hour. Then, paraffin was removed therefrom with xylene, and the sample was hydrated using ethanol.

2-7. Analysis of Expression of Gene Related to Lipid Metabolism by Real-Time PCR 1 mL of Trizol reagent (Invitrogen, USA) was added to about 50 mg to 100 mg of the excised liver, and the mixture was homogenized with a homogenizer, and then total RNA was extracted therefrom. From the RNA, cDNA was synthesized using a cDNA reverse transcription kit (QIAGEN, Japan).

Real-time quantitative PCR was performed using a 7500 Real-time Thermal Cycler (Applied Biosystems, USA) with SYBR Green (Applied Biosystems, USA) to measure gene expression. Genes and nucleotide sequences of PCR primers for respective genes are shown in Table 1 below. Real-time PCR was performed in a total volume of 20 μL including 2 μL of cDNA, 10 μL of 2×SYBR mix, 1 μL of a forward primer (100 pmol/μL), and 1 μL of a reverse primer (100 pmol/μL), and the remainder of $H_2O$.

TABLE 1

| Gene | Primer sequences |
|---|---|
| Fas | F GGAGGTGGTGATAGCCGGTAT |
|  | R TGGGTAATCCATAGAGCCCAG |
| ApoB | F CGTGGGCTCCAGCATTCTA |
|  | R TCACCAGTCATTTCTGCCTTTG |
| Cd36 | F TGGAGCTGTTATTGGTGCAG |
|  | R TGGGTTTTGCACATCAAAGA |
| Fabp | F GCTGCGGCTGCTGTATGA |
|  | R CACCGGCCTTCTCCATGA |
| β-actin | F GGCTGTATTCCCCTCCATCG |
|  | R CCAGTTGGTAACAATGCCATGT |

PCR amplification steps as described below were repeated for up to 40 cycles. After a hot start of 10 minutes at 95° C., cycles of denaturation for 15 seconds at 95° C., annealing for 30 seconds at 60° C., and extension for 30 seconds at 72° C. were repeated. Values were recorded after extension at every cycle.

After completion of all cycles, melting curve analysis was carried out to verify specificity of the primers. The results were analyzed using the One step system software v2.1 provided by Applied Biosystems.

2-8. Analysis of Inhibitory Effect on TNF-α in Alcoholic Steatosis Mice

The level of TNF-α in liver tissue was measured by using RT-PCR and ELISA as described above in Example 2-7 to analyze whether the amount of TNF-α induced by alcohol was reduced due to treatment of quercetin-3-O-β-D-xylopyranoside.

A commercially available ELISA kit purchased from R&D Systems (Minneapolis, Minn.) was used.

2-9. Analysis of Effect on Recovering Adiponectin in Alcoholic Steatosis Mice

Adiponectin, which is a major anti-inflammatory agent, is an adipose tissue-derived adipokine. It has been reported that adiponectin production is significantly reduced in patients chronically exposed to ethanol, and down-regulation of adiponectin content has an important pathological impact on the development of alcoholic steatosis disease (AFLD). Thus, a plasma level of adiponectin was analyzed by ELISA to evaluate the effect of quercetin-3-O-β-D-xylopyranoside on regulation of the adiponectin content.

Specifically, the plasma level of adiponectin was analyzed by using RT-PCR and ELISA in the same manner as the measurement of the TNF-α level in liver tissue as described above in Example 2-8.

2-10. Analysis of mRNA Level of MCP-1 and IL-1β

Monocyte chemoattractant protein 1 (MCP-1), called chemokine ligand 2 (CCL2), is one of the key chemokines that regulate pathogeneses of several diseases caused by monocyte infiltration. Meanwhile, interleukin 1 beta (IL1β), also known as a leukocytic endogenous mediator and a lymphocyte activating factor, is a member of the interleukin 1 family of cytokines. The cytokines are produced by activated macrophages at a damaged region of tissue.

Specifically, mRNA levels of MCP-1 and IL-1β were analyzed by using RT-PCR as described above in Example 2-8.

2-11. Analysis of Apoptosis in Liver Tissue by TUNEL Assay

DNA fragmentation characteristics of apoptosis were examined using a terminal deoxynucleotidyl transferase (TdT)-FragEL kit (Oncogene Research Products, San Diego, Calif.).

First, a tissue sample fixed in 4% paraformaldehyde was embedded in paraffin and sliced into 5 μm sections. Replicated sections were rehydrated and permeabilized with proteinase K (20 μg/mL) at 25° C. for 20 minutes. Subsequently, the sections were covered with 3% $H_2O_2$ for 5 minutes to inactivate endogenous peroxidase. After the sample was incubated in a TdT buffer solution (200 mM sodium-cacodylate, 30 mM Tris, 0.3 mg/mL BSA, 0.75 mM $CoCl_2$, pH 6.6) for 5 minutes, slides were covered with TdT and biotinylated dUTP and incubated in a humidified chamber at 37° C. for 1.5 hours. Negative controls were incubated with biotinylated dUTP in a TdT buffer solution without enzyme. Reactions were terminated by adding a stop buffer (0.5 M EDTA, pH 8.0) thereto at room temperature for 5 minutes. After blocking with 4% BSA, the slides were incubated with a streptavidin-horseradish peroxidase conjugate for 30 minutes. Subsequently, the sections were incubated in DAB at room temperature for 12 minutes and counterstained with methyl green. Apoptotic cells were identified by stained properties and morphological criteria (cell contraction, chromatin condensation and/or margination, and apoptotic bodies).

2-12. Expression of p-AMPKα, p-ACC, and CPT-1 in Liver Tissue

Expression of p-AMPKα, p-ACC, and CPT-1, which regulate intrahepatic lipid metabolism, was analyzed by western blot analysis to understand the mechanism involved in pathogenesis of alcoholic steatosis in detail. The specific western blot analysis method is as follows.

First, a mouse liver homogenate was prepared by using a RIPA buffer solution including a protease and tyrosine phosphatase inhibitor cocktail (Sigma). Protein concentrations of lysates were determined using a Bicinchoninic (BCA) Protein Assay Kit (Thermo Scientific, IL, USA) according to the manufacturer's instructions. Isolated soluble proteins (20 mg) were separated on an 8% to 15% SDS-polyacrylamide gel. The separated proteins were electroblotted on a nitrocellulose transfer membrane (Bio-Rad, Hercules, Calif., USA). The membrane was incubated with 5% non-fat dry milk for 1 hour and then probed for antigens using antibodies diluted to 1:1,000, and was incubated with anti-pAMPKα, anti-AMPKα, anti-PACC, anti-ACC, anti-CYP2E1, anti-CPT1a (Cell Signaling Technology), and anti-β-actin (Santa Cruz Biotechnology) at 4° C. for 18 hours. After washing three times for 10 minutes each, polyclonal anti-rabbit or mouse HRP-conjugated secondary antibody (Santa Cruz Biotechnology) linked to HRP-conjugate protein complex and expressed with Pierce ECL western blot substrate (Thermo Fisher Scientific) was added to the mixture. Band density was measured using ImageJ (National Institutes of Health, Bethesda, Md., USA) and expressed as a multiple relative to β-actin.

Example 3: Results and Analysis 3-1. Analysis of Effect of Quercetin-3-O-β-D-xylopyranoside on Body Weight and Organ Weight As a result of measuring body weights and organ weights of the mice according to Examples 2-1 and 2-2 as described above, there was no significant difference in the body weights among the groups when breeding was started, and no significant difference in body weight was observed in all groups fed with the alcohol liquid diet or treated with the drug.

Figure 1:
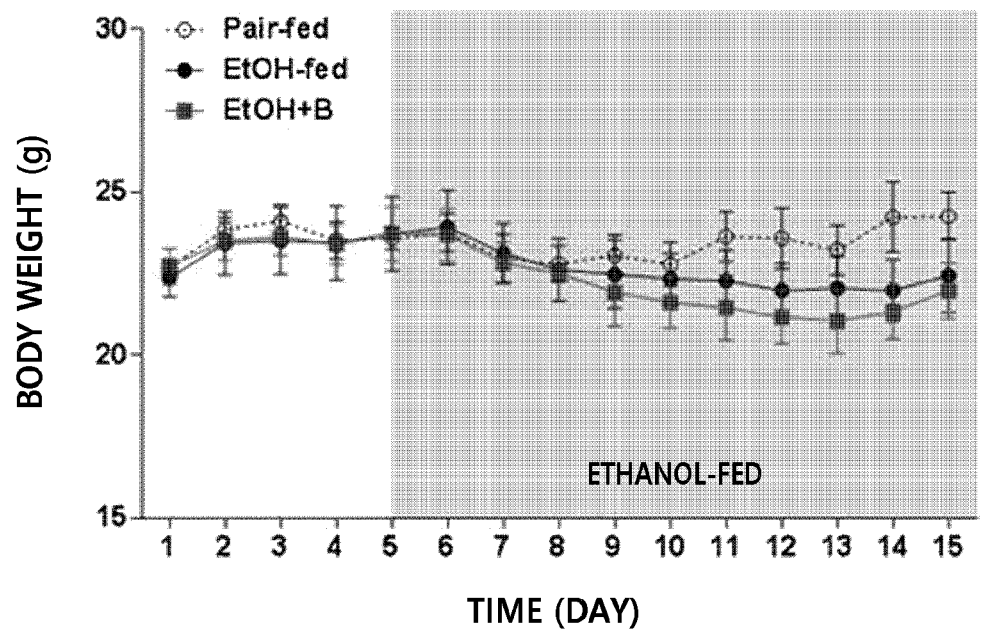
FIG. 1 is a graph illustrating changes in body weight of alcoholic fatty liver-induced mice and control mice for comparison therebetween.
Figure 2:
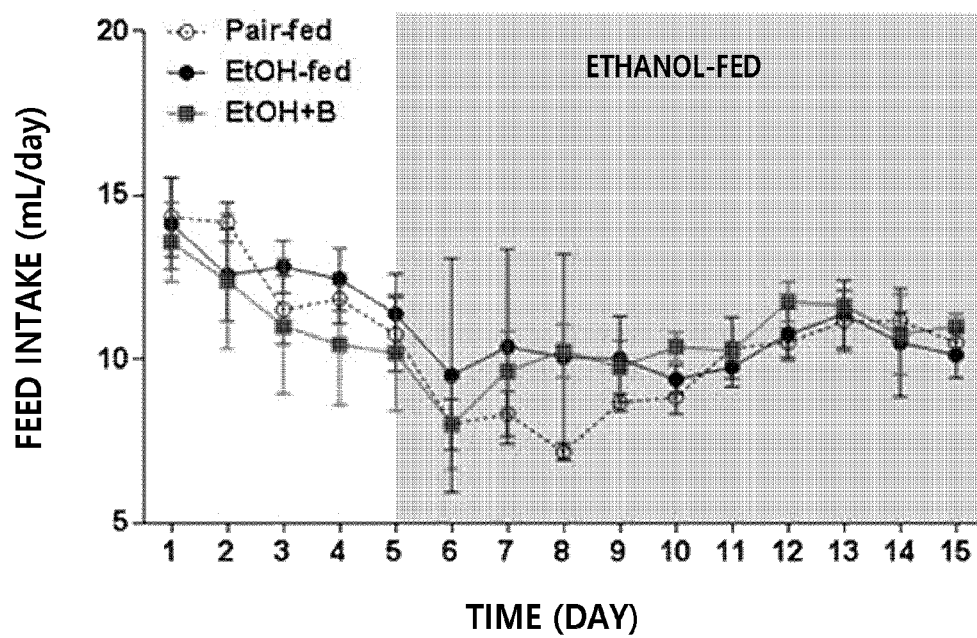
FIG. 2 is a graph illustrating changes in feed intake of alcoholic fatty liver-induced mice and control mice with respect to time.
Figure 3:
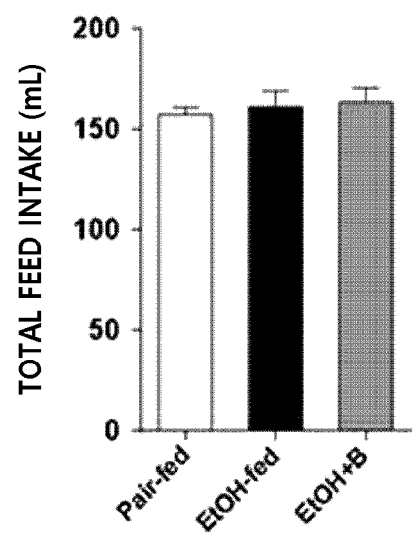
FIG. 3 is a graph illustrating total feed intake of alcoholic fatty liver-induced mice and control mice for comparison therebetween.

Specifically, when the 5% alcohol-containing liquid diet was fed together with administration of quercetin-3-O-β-D-xylopyranoside for 10 days after the 5 days of the liquid diet adaptation period, it was confirmed that the body weight was not affected. The EtOH+B group, a body weight gain was almost the same as those of the EtOH-fed group and the Pair-fed group even though the feed intake was the same as those of the EtOH-fed group and the Pair-fed group (FIG. 1), and thus it was confirmed that quercetin-3-O-β-D-xylopyranoside did not affect the feed intake and the body weight (FIGS. 2 and 3).

Figure 4:
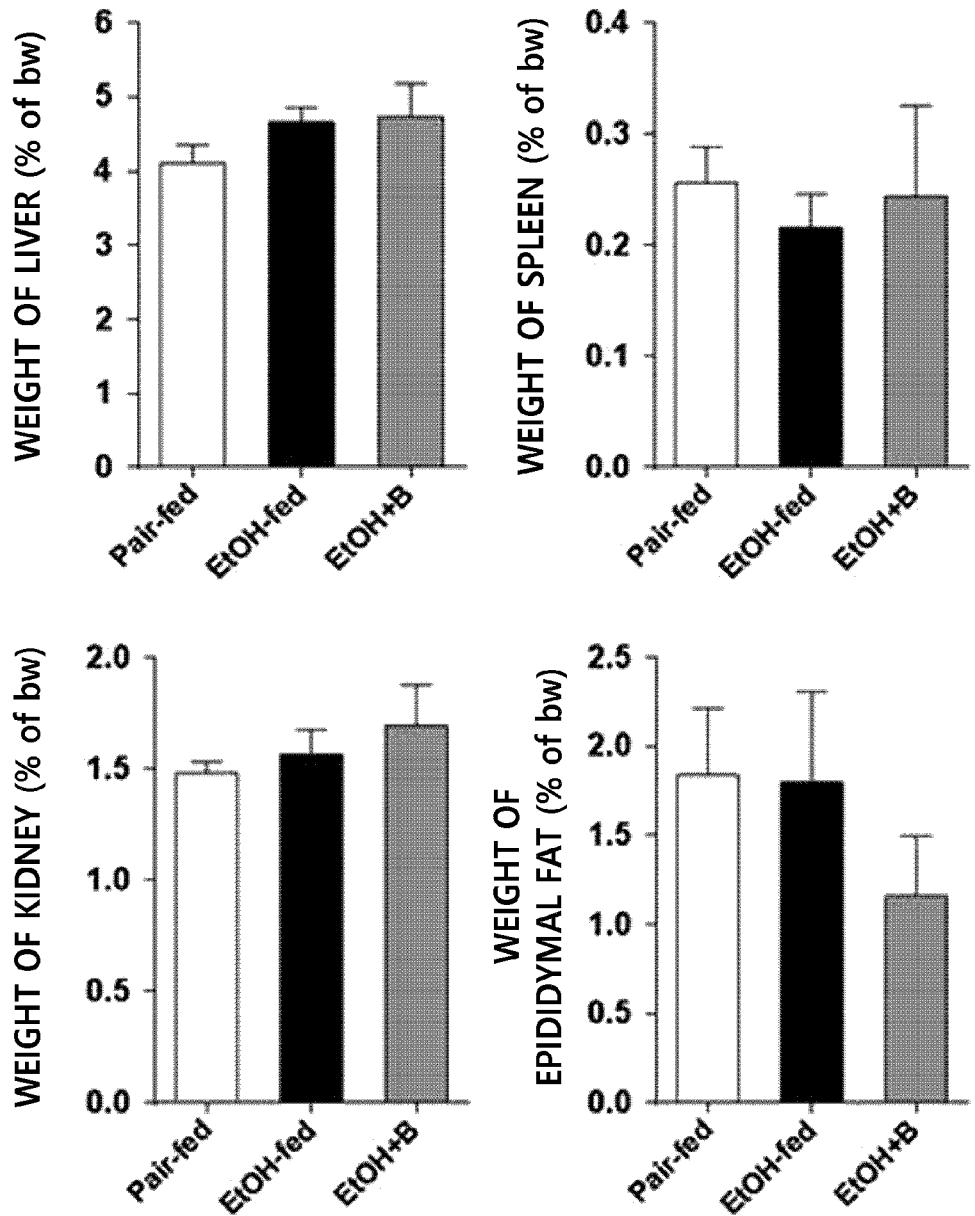
FIG. 4 is a graph illustrating weight of excised organs (liver, spleen, kidney, and epididymal fat) of alcoholic fatty liver-induced mice and control mice for comparison therebetween.

Meanwhile, as a result of measuring weight changes of the excised organs (liver, spleen, kidney, and epididymal fat) as percentages (%) of the body weight, no significant difference was observed between the EtOH+B group and the EtOH-fed group (FIG. 4). Therefore, it was confirmed that quercetin-3-O-β-D-xylopyranoside is a safe substance derived from natural products and exhibiting no toxicity to mice and internal organs.

Figure 5:
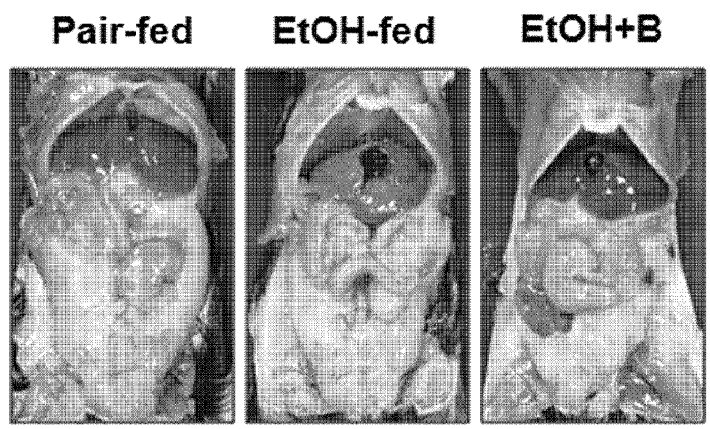
FIG. 5 shows photographs of dissected alcoholic fatty liver-induced mice and a dissected control mouse for visual observation of the degree of fat accumulation in the liver.

3-2. Analysis of Effect of Quercetin-3-O-β-D-xylopyranoside on Alcohol-induced Steatosis The effect of quercetin-3-O-β-D-xylopyranoside on steatosis induced by alcohol was examined First, when fatty liver is induced by an alcoholic diet, steatosis, accumulation of fat in the liver, occurs. As a result of dissection and visual observation of the mice, it was confirmed that a large amount of lipid components was accumulated in the mice of the EtOH-fed group, compared to the mice of the Pair-fed group. However, in the EtOH+B group administered with quercetin-3-O-β-D-xylopyranoside, an amount of lipid accumulated in the liver of the mice was significantly reduced, compared to the mice of the EtOH-fed group (FIG. 5).

In addition, as a result of identifying fat accumulation in tissue by H&E staining and Oil Red 0 staining described above in Examples 2-3 and 2-5, it was confirmed that lipid droplets were accumulated in liver tissue due to alcohol consumption in the EtOH-fed group, compared to the Pair-fed group, and the amount of lipid droplets in the liver tissue was significantly reduced in the EtOH+B group, compared to the EtOH-fed group (FIG. 6).

Also, as a result of measuring concentrations (mg/dL) of triglycerides in the blood and the liver and comparing the measured concentrations, it was confirmed that the concentrations of triglycerides in the blood and the liver were increased in the EtOH-fed group by alcohol consumption, compared to the Pair-fed group, but the concentrations of the triglycerides were significantly reduced in the EtOH+B group administered with quercetin-3-O-β-D-xylopyranoside (FIG. 7).

Therefore, it was confirmed that quercetin-3-O-β-D-xylopyranoside has the effects of preventing or treating steatosis by reducing the concentrations of triglycerides in the blood which were increased due to alcohol and inhibiting accumulation of triglycerides in the liver, having no toxicity and without affecting the feed intake and the body weight.

3-3. Analysis of Effect of Quercetin-3-O-β-D-xylopyranoside on Protecting Liver Against Alcohol-Induced Hepatitis, Hepatic Fibrosis, and Cirrhosis Expression of cytochrome P-450 2E1 (CYP2E1), known as a key enzyme of a microsomal ethanol oxidizing system (MEOS) accelerating ethanol oxidation and damaging the liver, was analyzed by tissue staining.

As a result, although the EtOH-fed group fed with ethanol showed a far higher CYP2E1 expression level than the Pair-fed group, indicating that hepatitis occurred, the EtOH+B group administered with quercetin-3-O-β-D-xylopyranoside exhibited a far lower CYP2E1 expression level than the EtOH-fed group, indicating that the hepatitis was alleviated (FIG. 8).

In addition, as a result of identifying the degree of progression of hepatic fibrosis in reticular fibers by tissue staining using Gomori Reticulum, the hepatic fibrosis progressed in the EtOH-fed group, compared to the Pair-fed group, but the progression of hepatic fibrosis was suppressed in the EtOH+B group administered with quercetin-3-O-β-D-xylopyranoside, compared to the EtOH-fed group (FIG. 9).

Meanwhile, as a result of measuring ALT and AST levels, which are indices of liver damage, in the blood and liver tissue, it was confirmed that the ALT and AST levels significantly increased in the EtOH-fed group, compared to the Pair-fed group, but the ALT and AST levels decreased in the EtOH+B group administered with quercetin-3-O-β-D-xylopyranoside, compared to the EtOH-fed group (FIG. 10).

Therefore, it was confirmed that quercetin-3-O-β-D-xylopyranoside has the effects of preventing and treating alcohol-induced hepatitis, hepatic fibrosis, and cirrhosis caused by continuous development of the hepatic fibrosis, indicating preventive and therapeutic effects on liver diseases and protective effects on the liver.

3-4. Effect of Quercetin-3-O-β-D-xylopyranoside on Expression of mRNA of Gene Related to Intrahepatic Lipid Metabolism Influence of quercetin-3-O-β-D-xylopyranoside on the expression of genes related to lipid metabolism was analyzed according to Example 2-7 as described above.

As a result, when gene expression levels of the Pair-fed group were regarded as 100%, the expression levels of the Fas gene were 1.4 times as much in the EtOH-fed group and 1.1 times as much in the EtOH+B group, which was lower than that of the EtOH-fed group. The expression levels of the ApoB gene were 1.8 times as much in the EtOH-fed group, showing almost no change, and 0.8 times as much in the EtOH+B group, which was lower than that of the control group. Also, the expression levels of the Cd36 gene were almost twice as much in the EtOH-fed group and 0.98 times as much in the EtOH+B group, which was similar to that of the control group. The expression levels of the Fabp gene were 1.2 times as much in the EtOH-fed group and 0.7 times as much in the EtOH+B group, which was far lower than that of the EtOH-fed group (FIG. 11).

Thus, since quercetin-3-O-β-D-xylopyranoside inhibits expression of the genes related to intrahepatic lipid metabolism, i.e., Fas, ApoB, Cd36, and Fabp genes, it may be confirmed that quercetin-3-O-β-D-xylopyranoside had positive effects on intrahepatic lipid metabolism and functions of mitochondria, resulting in preventive and therapeutic effects on a liver disease such as steatosis, hepatitis, hepatic fibrosis, and cirrhosis.

3-5. Identification of Inhibitory Effect on TNF-α in Alcoholic Steatosis Mice

Figure 12A:
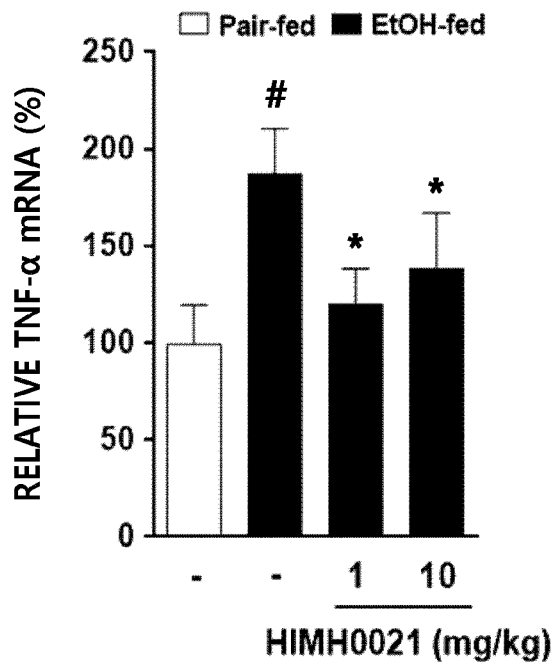
FIG. 12A is a graph illustrating expression levels of RNA of TNF-α in accordance with administration of quercetin-3-O-β-D-xylopyranoside (in FIGS. 12 to 16, HIMH0021 refers to quercetin-3-O-β-D-xylopyranoside).
Figure 12B:
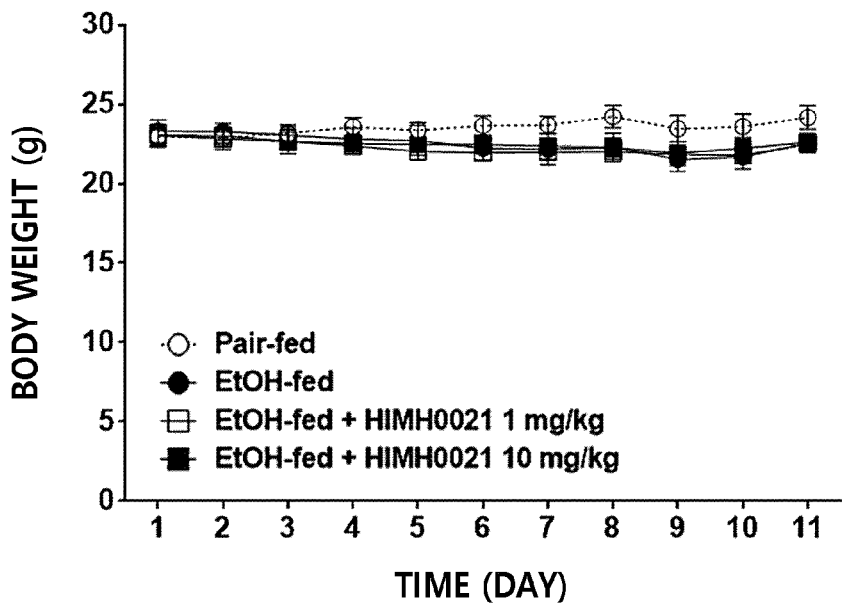
FIG. 12B is a graph illustrating body weight and feed intake of groups fed with quercetin-3-O-β-D-xylopyranoside and a control group.

As a result of identifying inhibitory effects on TNF-α in alcoholic steatosis mice, the expression level of RNA of TNF-α significantly increased in the alcohol-fed group, compared to the group fed with the normal liquid feed. However, in the groups administered with quercetin-3-O-β-D-xylopyranoside in amounts of 1 mg/kg and 10 mg/kg (HIMH0021 in FIGS. 12 to 16), the expression level of RNA of TNF-α was significantly inhibited (FIG. 12A). In addition, in the alcohol-fed group and in the group fed with alcohol and administered with quercetin-3-O-β-D-xylopyranoside, the body weight and the feed intake were slightly reduced, compared to the control group (FIG. 12B).

Figure 12C:
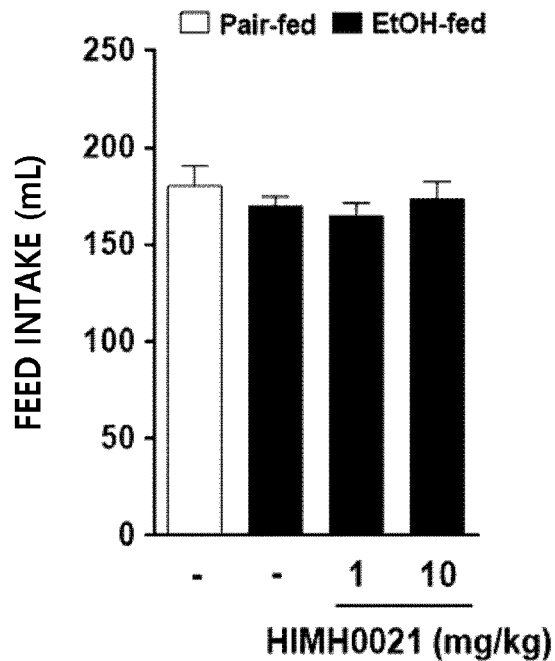
FIG. 12C is a graph illustrating total feed intake in accordance with administration of quercetin-3-O-β-D-xylopyranoside.
Figure 12D:
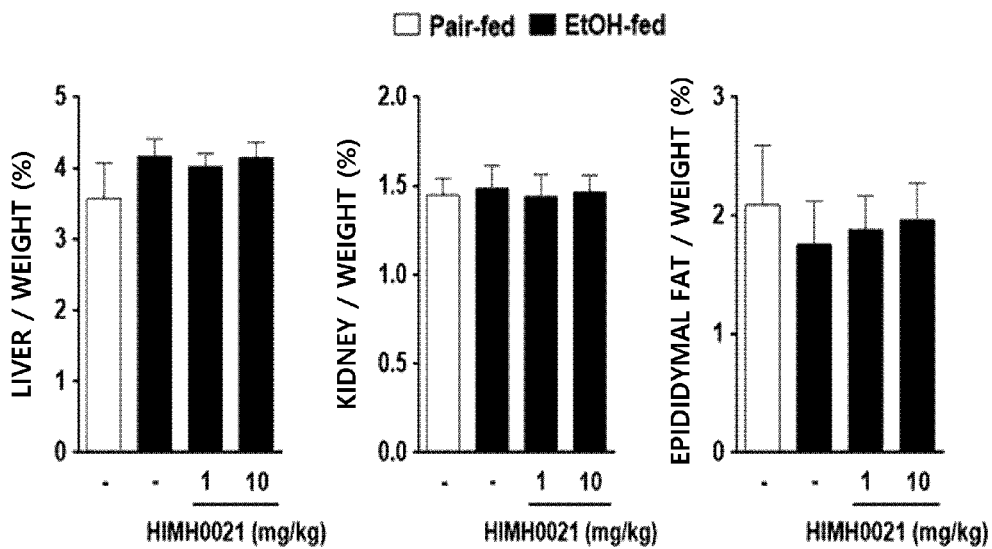
FIG. 12D is a graph illustrating weight percentage of excised organs (liver, kidney, and epididymal fat) in accordance with administration of quercetin-3-O-β-D-xylopyranoside.

Meanwhile, there was no change in the feed intake in the Pair-fed group, the alcohol-fed group, and the alcohol+quercetin-3-O-β-D-xylopyranoside-administered group, and there was no relative change in the weights of the liver, the kidney, and epididymal fat (FIGS. 12C and 12D).

Thus, it was confirmed that the intake of quercetin-3-O-β-D-xylopyranoside may significantly reduce the expression level of TNF-α increased by alcohol consumption.

Figure 13:
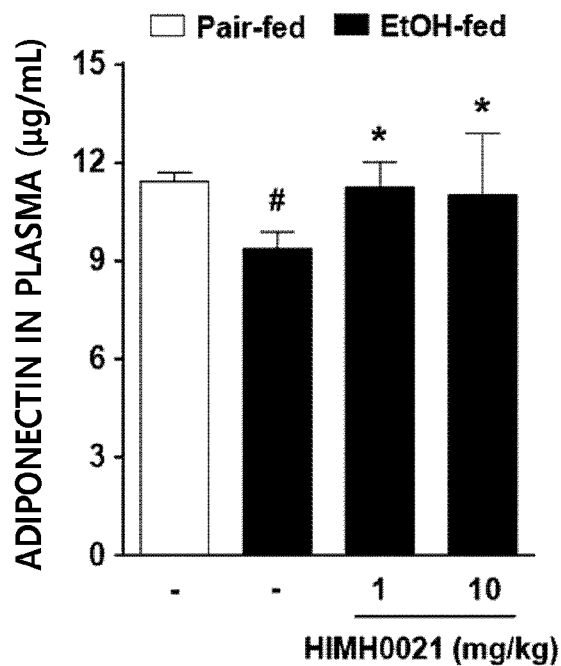
FIG. 13 is a graph for identifying an adiponectin recovery effect in alcoholic fatty liver mice.

3-6. Identification of Effect on Recovering Adiponectin in Alcoholic Steatosis Mice As a result of identifying effects on recovering adiponectin in the alcoholic steatosis mice, it was confirmed that the adiponectin plasma level significantly decreased in the alcohol-fed group, as shown in FIG. 13. In contrast, the plasma adiponectin level was significantly recovered in the alcohol+quercetin-3-O-β-D-xylopyranoside-administered group. Thus, it was confirmed that treatment of quercetin-3-O-β-D-xylopyranoside may restore the concentration of adiponectin reduced by alcohol.

3-7. Identification of mRNA Level of MCP-1 and IL-1β

Figure 14:
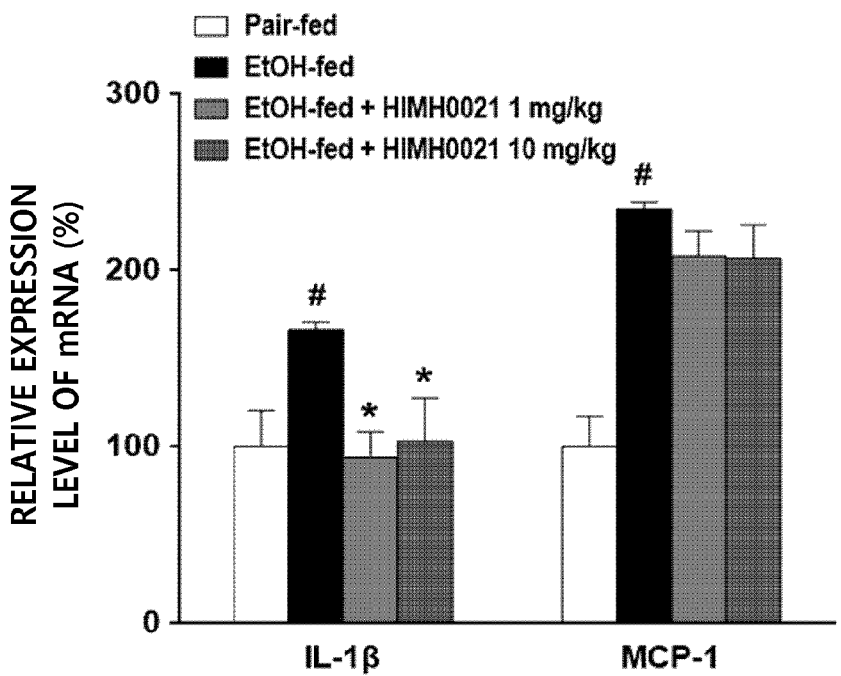
FIG. 14 is a graph for identifying mRNA levels of MCP-1 and IL-1β.

The alcohol-fed group showed higher mRNA levels of MCP-1 and IL-1β than the control group as shown in FIG. 14. On the contrary, it was confirmed that the mRNA levels of the two factors were significantly reduced in the alcohol+quercetin-3-O-β-D-xylopyranoside-administered group.

Therefore, it was confirmed that the effects of quercetin-3-O-β-D-xylopyranoside on treating the alcoholic steatosis and protecting the liver involve decreases in the expression levels of MCP-1 and IL-1β.

Figure 15:
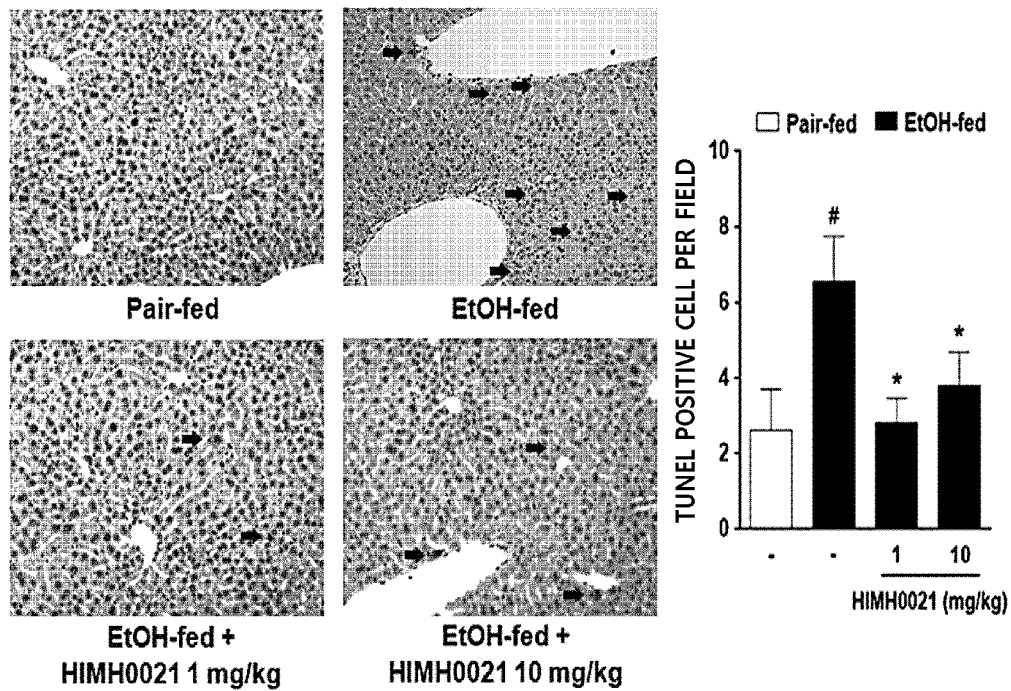
FIG. 15 illustrates apoptosis inhibiting effects in liver tissue evaluated by TUNEL assay.

3-8. Identification of Apoptosis-Inhibiting Effect in Liver Tissue by TUNEL Assay As a result of analyzing apoptosis in liver tissue by TUNEL assay, the number of apoptotic cells of the alcohol-fed group was higher than that of the normal control group as shown in FIG. 15. In contrast, the degree of apoptosis was significantly reduced in the alcohol+quercetin-3-O-β-D-xylopyranoside-administered group, compared to the experimental group fed with only alcohol.

Thus, it was confirmed that quercetin-3-O-β-D-xylopyranoside has the effect of significantly inhibiting apoptosis in liver tissue induced by alcohol consumption.

3-9. Identification of Expression Level of p-AMPKα, p-ACC, and CPT-1 in Liver Tissue As a result of analyzing expressions of p-AMPKα, p-ACC, and CPT-1, which regulate intrahepatic lipid metabolism, by western blot, it was confirmed that lipid metabolism-regulating proteins were inhibited due to alcohol consumption, thereby promoting alcoholic steatosis.

Figure 16A:
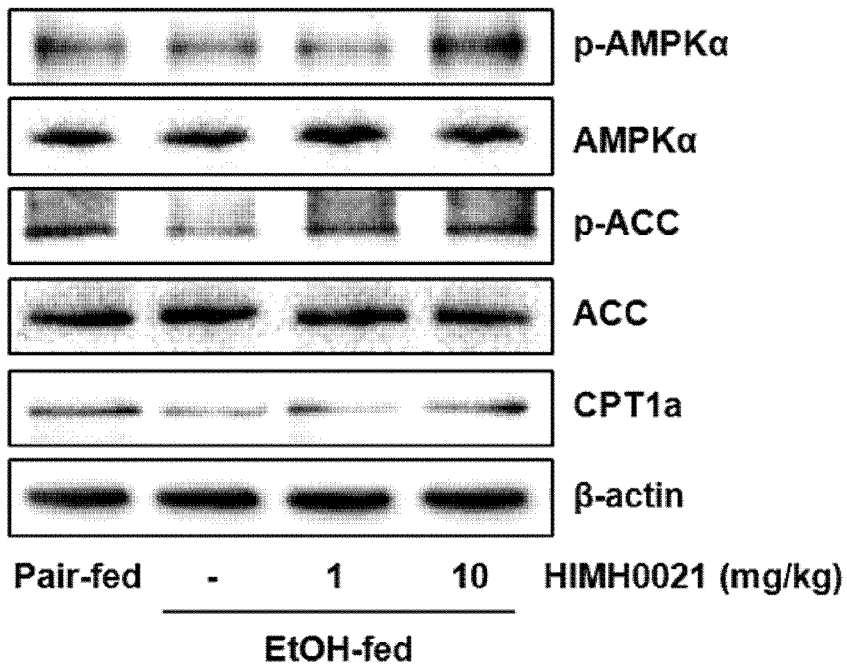
FIGS. 16A and 16B illustrate expression levels of p-AMPKα, p-ACC, and CPT-1 in liver tissue.
Figure 16B:
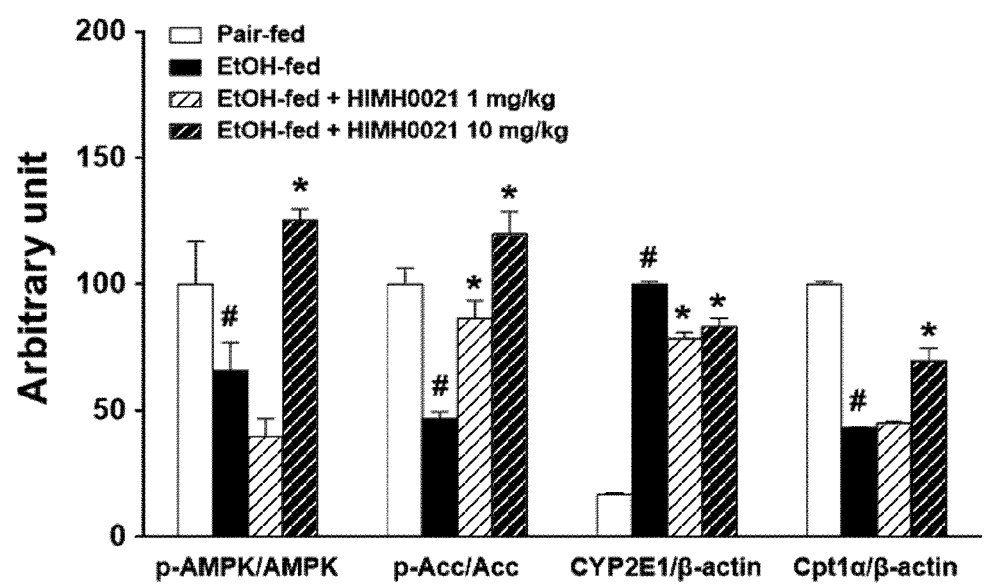

Specifically, as shown in FIGS. 16A and 16B, while there was no difference in expression levels of AMPK protein among the groups, the expression level of pAMPK was significantly increased in the group treated with 10 mg/kg of quercetin-3-O-β-D-xylopyranoside. Therefore, it was confirmed that quercetin-3-O-β-D-xylopyranoside increases phosphorylation of AMPK in a concentration-dependent manner and activates the AMPK signaling pathway.

Meanwhile, the p-ACC and CPT-1 levels of the alcohol-fed group were significantly lower than those of the normal control group. In contrast, the p-ACC and CPT-1 levels were significantly restored in liver tissue of the group administered with quercetin-3-O-β-D-xylopyranoside.

Therefore, it was confirmed that quercetin-3-O-β-D-xylopyranoside significantly restores the p-ACC and CPT-1 levels in liver tissue which were decreased due to alcohol consumption, thereby exhibiting therapeutic effects on alcoholic steatosis and protecting effects on the liver.

While the present invention has been described with reference to the particular illustrative embodiments, it will be understood by those skilled in the art to which the present invention pertains that the present invention may be embodied in other specific forms without departing from the technical spirit or essential characteristics of the present invention. Therefore, the embodiments described above are considered to be illustrative in all respects and not restrictive. Furthermore, the scope of the present invention should be defined by the appended claims rather than the detailed description, and it should be understood that all modifications or variations derived from the meanings and scope of the present invention and equivalents thereof are included in the scope of the present invention.

ACKNOWLEDGEMENT

This study was supported by the Forest Science and Technology Research and Development Project (FTIS 2017022B10-1719-BA01) of the Korea Forest Service (Korea Forestry Promotion Institute).

The invention claimed is:

1. A method of treating alcoholic steatosis, the method comprising administering a pharmaceutical composition comprising an effective amount of quercetin-3-O-β-D-xylopyranoside to a subject.

2. The method according to claim 1, wherein the treating is performed by inhibiting accumulation of fat in the liver and suppressing expression of genes related to intrahepatic lipid metabolism.

3. The method according to claim 2, wherein the genes related to intrahepatic lipid metabolism comprise at least one gene selected from the group consisting of Fas, ApoB, Cd36, and Fabp.

4. The method according to claim 1, wherein the quercetin-3-O-β-D-xylopyranoside is derived from *Acer tegmentosum maxim*.

5. A method of alleviating alcoholic steatosis, the method comprising administering a health functional food comprising an effective amount of quercetin-3-O-β-D-xylopyranoside to a subject.

6. The method according to claim 5, wherein the alleviating is performed by inhibiting accumulation of fat in the liver and suppressing expression of genes related to intrahepatic lipid metabolism.

7. The method according to claim 6, wherein the genes related to intrahepatic lipid metabolism comprise at least one gene selected from the group consisting of Fas, ApoB, Cd36, and Fabp.

8. The method according to claim 5, wherein the quercetin-3-O-β-D-xylopyranoside is derived from *Acer tegmentosum maxim*.

* * * * *